United States Patent
Moaddel et al.

(10) Patent No.: US 7,417,014 B2
(45) Date of Patent: Aug. 26, 2008

(54) DILUTION THICKENED PERSONAL CLEANSING COMPOSITION

(75) Inventors: Teanoosh Moaddel, Watertown, CT (US); Syed Husain Abbas, Seymour, CT (US); Kimberly Ozkan-Bal, Middlebury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 114 days.

(21) Appl. No.: 11/423,787

(22) Filed: Jun. 13, 2006

(65) Prior Publication Data

US 2007/0287648 A1 Dec. 13, 2007

(51) Int. Cl.
C11D 1/02 (2006.01)
C11D 1/66 (2006.01)
C11D 1/83 (2006.01)
C11D 3/37 (2006.01)
C11D 17/08 (2006.01)

(52) U.S. Cl. .............. 510/120; 510/127; 510/140; 510/155; 510/156; 510/159; 510/406; 510/417; 510/421; 510/426; 510/475; 424/401; 424/70.11; 424/70.19; 424/70.22; 424/70.31

(58) Field of Classification Search .............. 510/120, 510/127, 140, 155, 156, 159, 406, 417, 421, 510/426, 475; 424/401, 70.11, 70.19, 70.22, 424/70.31
See application file for complete search history.

(56) References Cited

U.S. PATENT DOCUMENTS

| | | |
|---|---|---|
| 4,898,690 A | 2/1990 | Bitter et al. |
| 5,130,056 A | 7/1992 | Jakobson et al. |
| 5,372,751 A | 12/1994 | Rys-Cicciari et al. |
| 5,906,973 A | 5/1999 | Ouzounis et al. |
| 6,022,547 A | 2/2000 | Herb et al. |
| 6,087,320 A | 7/2000 | Urfer et al. |
| 6,150,320 A | 11/2000 | McDonell et al. |
| 6,440,912 B2 | 8/2002 | McGee et al. |
| 6,524,594 B1 | 2/2003 | Santora et al. |
| 6,617,293 B2 | 9/2003 | Chen |
| 6,919,303 B2 | 7/2005 | Pham et al. |
| 2002/0002123 A1 | 1/2002 | McGee et al. |
| 2004/0053804 A1* | 3/2004 | Yomogida et al. ........... 510/424 |
| 2005/0008605 A1 | 1/2005 | L'Alloret |
| 2005/0058719 A1 | 3/2005 | Ramirez et al. |
| 2005/0112160 A1 | 5/2005 | Tanner et al. |

FOREIGN PATENT DOCUMENTS

| | | |
|---|---|---|
| DE | 44 16 566 | 11/1995 |
| DE | 195 04 192 | 8/1996 |
| EP | 0 246 854 | 11/1987 |
| EP | 0 281 027 | 9/1988 |
| EP | 0 288 919 | 11/1988 |
| EP | 0 291 262 | 11/1988 |
| EP | 0 346 993 | 12/1989 |
| EP | 0 379 658 | 8/1990 |
| EP | 0 542 526 | 5/1993 |
| EP | 0 572 776 | 12/1993 |
| EP | 1 066 827 | 1/2001 |
| JP | 63-270533 | 11/1988 |
| WO | 92/08440 | 5/1992 |
| WO | 93/25650 | 12/1993 |
| WO | 94/03146 | 2/1994 |
| WO | 94/03152 | 2/1994 |
| WO | 94/16680 | 8/1994 |
| WO | 03/094874 | 11/2003 |
| WO | WO 03/094874 | * 11/2003 |

OTHER PUBLICATIONS

International Search Report, PCT/EP2007/052001, mailed Jul. 4, 2007, 3 pp.
"Partitioning of hydrophobic amino acids and oligopeptides in aqueous two-phase system containing self-aggregating block copolymer—Effects of temperature, salts and surfactants", Journal of Chromatography A, vol. 761, No. 1-2, pp. 91-101, (abstract only), 1997 no month given.
"Phase Behavior of a PEO-PPO-PEO Triblock Copolymer in Aqueous Solutions; Two Gelation Mechanisms", Macromolecular Research, vol. 10, No. 6, pp. 325-331 (2002), Nov. 7, 2002.
"Rheology of Pluronic Solutions Mixed with a Non-Ionic Diol Surfactant", XIIIth International Congress on Rheology, Cambridge, UK, 2000, pp. 3-304 to 3-306, 2000 no month given.

* cited by examiner

*Primary Examiner*—Brian P Mruk
(74) *Attorney, Agent, or Firm*—Alan A. Bornstein

(57) ABSTRACT

A liquid or flowable cleansing composition is described that contains high levels of anionic and nonionic surfactants and that show a substantial increase in viscosity upon dilution with water. The cleansing composition also contains water soluble EO/PO block copolymer(s).

11 Claims, No Drawings

DILUTION THICKENED PERSONAL CLEANSING COMPOSITION

BACKGROUND OF THE INVENTION

1. Field of the Invention

The present invention relates to detergent compositions suitable for topical application for cleansing the human body, such as the skin and hair. In particular, it relates to dilution thickened personal cleansing compositions.

2. Background of the Art

Commercially available liquid personal washing compositions, i.e. shower gels, facial and hand cleansers that are low in viscosity are generally applied to the skin with an implement to enable vigorous cleansing. Such implements include a pouf, sponge, cloth or brush and the like. These low viscosity products are advantageous since they are easily dispensed and can be easily applied to or with such implements. Frequently however implements are not available for use or are inconvenient to use depending on the circumstances. Surprisingly an easily dispensed, low viscosity cleansing product has been discovered that thickens appreciably with water dilution to create a substantially thickened product with sufficient solubility/dispersibility in water. This product shows enhanced adhesion to the skin and acts as in-situ implement which obviates the need for a separate implement for the vigorous cleansing of the skin.

Dilution thickening cleansers are known that have liquid crystal structure. PCT publication no. WO 94/16680 discloses the use of an electrolyte and high levels of water and synthetic detergents including ethoxylated alcohols to form a viscous structured liquid crystalline lamellar phase in the undiluted product. Polaxamers are generally mentioned as optional components.

U.S. Pat. No. 6,919,303 issued to Pham on Jul. 19, 2005 discloses a process for making a single phase dilution thickening composition comprising electrolyte and defined associative thickeners including: Rewoderm® LIS75, (PEG-200 glyceryl tallowate); Rheodol® (tristearate modified PEG) and Elfacos® T212 (carbamic acid diester of the polyoxypropylene, polyoxyethylene ether of the fatty alcohols derived from palm kernel oil); ethylene glycol ether of ethylene cellulose (hydroxyethyl ethylcellulose) such as Elfacos® CD481; or ethyl glycol ether of methyl cellulose, such as Methocel® 40-10.

U.S. Pat. No. 6,617,293 issued to Chen on Sep. 9, 2003 discloses a concentrated liquid soap composition that readily increases in viscosity upon dilution with water, the concentrated liquid soap composition containing an amine oxide surfactant; an anionic surfactant; an electrolyte; water; and a buffering agent, sufficient to maintain the pH of the composition between about 8 and about 10.

BRIEF DESCRIPTION OF THE INVENTION

In one aspect of the invention is a dilution thickening cleansing composition in the form of either a solution, dispersion, emulsion, or microemulsion, including but not limited to:
a. about 20 to 60% by wt. of total anionic surfactant(s);
b. about 5 to 50% by wt. of total nonionic surfactant(s);
c. about 1 to 80% by wt. of total water soluble block copolymer(s);
d. about 0 to 40% by wt. of water,
e. less than 50% by volume of a liquid crystal structured phase; and
f. preferably wherein the pre-dilution viscosity of the cleansing composition is in the range of about 1 Pa·s to 25,000 Pa·s at $10^{-1}s^{-1}$ at 25° C. as measured using the Standard Viscosity Method described below.

In another aspect of the invention is a prefilled dispenser packaged product for dispensing a thickened cleansing composition, comprising:
a. a chamber with at least one outlet; and
b. the inventive cleansing composition contained within the chamber.

DETAILED DESCRIPTION OF THE INVENTION

In one aspect of the invention is a dilution thickening cleansing composition in the form of either a solution, dispersion, emulsion, microemulsion, or liquid crystal dispersion, including but not limited to:
a. about 20 to 60% by wt. of total anionic surfactant(s); (preferably having a minimum of 20 or 30 and maximum of 40 or 50% by wt.)
b. about 5 to 50% by wt. of total nonionic surfactant(s); (preferably having a minimum of 20 or 30 and maximum of 40 or 50% by wt.)
c. about 1 to 80% by wt. of total water soluble block copolymer(s) (preferably having a minimum of 5, 10 or 15 and maximum of 45 or 35% by wt.); wherein the ratio range of nonionic surfactants to block copolymers is in the range of 0.5 to 2;
d. about 0 to 40% by wt. of water; (preferably having a minimum of 0.05, 0.1, 0.5, 1, 2, 3, 4 or 5 and maximum of 20, 25 or 30% by wt.);
e. less than 50% by volume of a liquid crystal structured phase; and
f. preferably wherein the viscosity of the cleansing composition is in the range of about 1 Pa·s to 25,000 Pa·s at $10^{-1} s^{-1}$ at 25° C. as measured using the Standard Viscosity Method described below.

Advantageously the inventive cleansing composition has at least one phase with a delta viscosity value of greater than about 10,000 Pa·s (preferably a maximum of about 50K, 75K or 100000) when blended with an equal amount by weight of water using the Standard Viscosity Method.

Preferably the composition further includes about 0 to 10% by wt. of total hydrophilic emollient(s) and about 0 to 10% by wt. of total hydrophobic emollient(s), wherein the combined concentration of the hydrophilic emollient(s) and hydrophobic emollient(s) is not zero.

In a preferred embodiment, the water soluble block copolymer(s) has a mean number average molecular weight range of from about 1,000 to 20,000 (preferably having a minimum of 2,000 or 3,000 and maximum of 7,000 or 8,000). Preferably at least one of the water soluble block copolymer(s) has the structure according to formula I:

(I) HO(CH2CH2O)x(CH(CH3)CH2O)y(CH2CH2O)x H 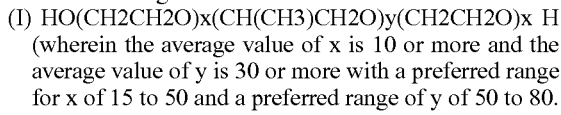
(wherein the average value of x is 10 or more and the average value of y is 30 or more with a preferred range for x of 15 to 50 and a preferred range of y of 50 to 80.

Advantageously the inventive composition has a ratio of total hydrophobic to total hydrophilic emollient(s) of from 10 to 0.1. (preferably the ratio is in the range of 8 to 0.12 and more preferably in the range of 6 to 0.16). Preferably the hydrophobic emollient(s) (skin conditioning agent(s)) are selected from glyceride oils, mineral oils, silicone oils or blends and derivatives thereof.

In a preferred embodiment, the anionic surfactants are selected from the class of surfactants with a Krafft temperature of less than 20° C. Examples include but are not limited to SLES, ALS, Amine Oxides, and betaines and the like. Preferably the ratio of total amphoteric surfactant to total anionic surfactant can range from 1 to 10.

Advantageously the inventive composition further includes at least 0.1% by wt. of an active agent.

In another aspect of the invention is a prefilled dispenser and packaged product for dispensing a thickened cleansing composition, comprising:
a. a chamber with at least one outlet; and
b. the inventive cleansing composition contained within the chamber.

Advantageously the dispenser further contains an inlet adapted for admitting water into the chamber.

Isotropic Solution, Microemulsion or Emulsion Compositions

In contrast to liquid crystal structured surfactant solutions described below, the inventive solution, dispersion, emulsion and microemulsion compositions are substantially isotropic in nature. In the case where the inventive composition is an emulsions, it is useful to note that emulsions are dispersions of two or more immiscible phases. These phases can be liquid, solid or liquid crystalline in nature, and be isotropic or anisotropic in nature. The inventive composition is further characterized in a preferred embodiment as an isotropic solution but may contain up to 1, 2, 3, 4, 5, 10, 15, 20, 30, 40 or 50% by volume of dispersed components where only the dispersed components have ordered liquid crystalline structures as measured by the procedure outlined below or its equivalent.

Ordered Liquid Crystalline Compositions:

The rheological behavior of all surfactant solutions, including liquid cleansing solutions, is strongly dependent on the microstructure, i.e., the shape and concentration of micelles or other self-assembled structures in solution. When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. Although not wishing to be bound to the following theory, it is believed that a cubic phase forms when the substantially isotropic composition of the invention is diluted with water, thus causing a significant increase in viscosity for the inventive composition.

Surfactants:

Surfactants are an essential component of the inventive cleansing composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The cleansing composition of the present invention contains one or more anionic detergents. Anionic surfactants are preferably used at levels as low as 20 or 30% by wt. and at levels as high as 40, 50 or 60% by wt. The anionic detergent active which may be used may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

$$R\;C-O(O)-C(X)H-C(Y)H_2-(OCH-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Nonionic Surfactants

One or more nonionic surfactants are used in the cleansing composition of the present invention. Nonionic surfactants are preferably used at levels as low 5, 10, 15, 20 or 30% by wt. and at levels as high as 40 or 50% by wt. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include fatty acid/alcohol ethoxylates having the following structures
a) HOCH2(CH2)n(CH2CH2O)x H or
b) HOOC(CH2)m(CH2CH2O)y H;

where m, n are independently<18; and x, y are independently>1. preferably m, n are independently 6 to 18; x, y are independently 1 to 30;
HOOC(CH2)i-CH=CH—(CH2)k(CH2CH2O)z H;

where i, k are independently 5 to 15; and z is independently 5 to 50. preferably i, k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Water Soluble Block Copolymer

An essential component of compositions according to the invention is a water soluble block copolymer. This is a block copolymer based on polyethyleneoxide (EO) and polypropyleneoxide (PO) blocks. The number average molecular weight of the block copolymer is suitably in the range 1000-20000 unified atomic mass units or more, preferably in the range 1000-10000, more preferably in the range 1000-8000, most preferably in the range 2000-7000.

The mean molecular weight is suitably measured by determining the hydroxyl number for the polymer, then transforming this into molecular weight. This corresponds to a number based mean molecular weight.

Each block of EO in the surface active block copolymer molecule suitably consists of 2 or more of the respective monomer units, preferably of 4 or more, more preferably of 6 or more, even more preferably of 10 or more and most preferably of 15 or more monomer units. Each block of PO in the surface active block copolymer molecule suitably consists of 10 or more of the respective monomer units, preferably of 20 or more, more preferably of 30 or more, even more preferably of 40 or more and most preferably of 50 or more monomer units.

Suitable EO/PO block copolymers according to formula I have the; CTFA designation Poloxamer. These are commercially available under the trade name "Pluronic" from BASF (New Jersey and Germany).
A) HO(CH2CH2O)x(CH(CH3)CH2O)y(CH2CH2O)x H CH3

Suitably, the mean value of x in formula A is 4, 6, 8, 10 or 15 or more. Suitably, the mean value of y is 20, 30, 40 or 50 or more.

Suitable EO/PO block copolymers according to formula B have the CFTA designation Poloxamine and are commercially available under the trade name "Tetronic" from BASF.
B)   HO(CH2CH2O)a(CH(CH3)CH2O)b)2-N—CH2—CH2-N((OCH2CH(CH3))b(OCH2CH2)aOH)2

Suitably, the mean value of a is 2 or more, preferably 4 or more, more preferably 8 or more, even more preferably 20 or 25 more and most preferably 40 or more. The mean value of b is 6 or more, preferably 9 or more, more preferably 11 or and most preferably 15 or more.

In formula A, the degree of polymerization, x, is indicated as the same for each polyethyleneoxide block. This is also the case in formula B for a and b for the EO and PO blocks respectively. For the sake of clarity, it should be explained that these degrees of polymerization are mean values and are approximately the same rather than identical for any particular formula. This is a result of the polymerization methods used for production of the compounds and known to those skilled in the art of polymer synthesis.

Suitably, the level of water soluble block copolymer is from 1 to 80% by weight of the composition, preferably from 2, 3, 4 or 5%, preferably having a maximum concentration of 50, 60 or 70%.

Amphoteric Surfactants

One or more amphoteric surfactants may be used in this invention. Amphoteric surfactants are preferably used at levels as low as 1, 2, 3, 4, or 5% by wt. and at levels as high as 20, 30 or 40% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

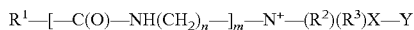

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —CO2— or —SO3—

Suitable amphoteric surfactants within the above general formula include simple betaines of formula:

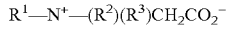

and amido betaines of formula:

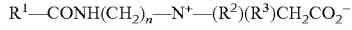

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

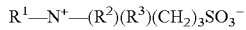

Or

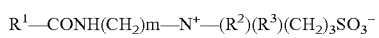

where m is 2 or 3, or variants of these in which —(CH2)3SO3— is replaced by

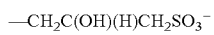

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

The combination of total anionic, nonionic, amphoteric surfactants and water-soluble block co-polymer(s) should preferably be more than 40% in the mixture.

Cationic Skin Conditioning Agents

A useful component in compositions according to the invention is a cationic skin feel agent or polymer, such as for example cationic celluloses. Cationic polymers are preferably used at levels as low as about 1 to 2% and at levels as high as about 4 to 5% by wt. Cationic cellulose is available from Amerchol Corp. (Edison, N.J., U.S.A.) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., U.S.A.) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Cationic Surfactants

One or more cationic surfactants may also be used in the cleansing composition. Cationic surfactants may be used at levels as low as about 1 to 2% and at levels as high as 3, 4 or 5% by wt.

Examples of cationic detergents are the quaternary ammonium compounds such as alkyldimethylammonium halogenides. Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage. Preferably strongly ionizing salts, otherwise known as electrolytes, will be present at less than 3, 2 or 1% by wt.

Antioxidants such as, for example, butylated hydroxytoluene (BHT) and the like may be used advantageously in amounts of about 0.01% or higher if appropriate.

Moisturizers that also are Humectants such as polyhydric alcohols, e.g. glycerine and propylene glycol, and the like; and polyols such as the polyethylene glycols and the like may be used. Humectants are preferably present at about 2, 5, 7, 8 or 10% by wt.

Hydrophobic and/or hydrophilic emollients or humectants mentioned above may be used. Hydrophobic emollients are preferably present in a concentration greater than about 2, 3, 5, 7, 8 or 10% by weight.

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients (also considered conditioning compounds according to the invention) include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) mixtures of any of the foregoing components, and the like.

Preferred conditioning agents are selected from mineral, silicone and vegetable oil(s) or blends and derivatives thereof. Further preferred emollients are triglyceride oils such as sunflower seed oil.

Optional Active Agents

Advantageously, active agents other than conditioning agents such as emollients or moisturizers defined above may be added to the cleansing composition in a safe and effective amount during formulation to treat the skin during the use of the product. These active ingredients may be advantageously selected from antimicrobial and antifungal actives, vitamins, anti-acne actives; anti-wrinkle, anti-skin atrophy and skin repair actives, skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0.01% to about 50%, more preferably from about 0.05% to about 25%, even more preferably 0.1% to about 10%, and most preferably 0.1% to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g. such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and, genistine mixtures thereof and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLES

Examples of cleansing compositions A-C (inventive examples 1-3 below) were prepared according to the procedure below and their viscosity and phase behavior were evaluated compared to comparative case CC (example 5). The inventive compositions were found to provide a significant increase in delta viscosity compared to the comparative example. Prophetic example 4 further illustrates five suitable compositions, D to H, according to the invention.

Preferably the combined active level of nonionic, anionic and amphoteric surfactants(s) is more than 50% by wt. in order to allow the composition to develop the required viscosity after dilution with water.

Example 1 (Inventive)

An inventive sample A was formulated according to Table 1 below.

TABLE 1

| Concentration | Component |
|---|---|
| 24.23% | Brij 98 (1) |
| 24.23% | Pluronic P-105 (2) |
| 40.06%[70% active] | SLES (3) |
| 3.69% | Water |
| 0.18% | Preservative (4) |
| 1.69% | Sunflower Seed Oil |
| 5.92% | Glycerin |
| 100% | Total |

Notes:
(1) C18:1(EO)20
(2) (EO)37(PO)56(EO)37
(3) Sodium lauryl ether sulfate (2EO) aq. soln.
(4) 1:1 EDTA and EHDP
Initial Viscosity of sample A is 4 Pa·s at $10^{-1}$ $s^{-1}$ at 25 C. as measured by an Ares Rheometer, 25 mm parallel plate.
Sample A with 50% water added (50 grams of A and 50 grams water) separated into two phases one of which had a viscosity of 24344 Pa·s at $10^{-1}$ $s^{-1}$ at 25 C. as measured by an Ares Rheometer, 25 mm parallel plate. Sample A had a delta viscosity (difference of the pre-dilution viscosity and the highest viscosity phase) at $10^{-1}$ $s^{-1}$ at 25 C. of 24340 Pa·s.

Example 2 (Inventive)

An inventive sample B was formulated according to Table 2 below.

TABLE 2

| Concentration | Component |
|---|---|
| 26.30% | Brij 98 |
| 26.30% | Pluronic P-105 |
| 43.40% [70% active amount] | 70% Active SLES/30% Water |
| 4.00% | DI Water |
| 100% | Total |

Initial Viscosity of sample B is 3 Pa·s at $10^{-1}$ $s^{-1}$ at 25 C. as measured by an Ares Rheometer, 25 mm parallel plate.
Sample B with 50% water added (50 grams of B and 50 grams water) has a viscosity of 19503 Pa·s at $10^{-1}$ $s^{-1}$ at 25 C. as measured by an Ares Rheometer, 25 mm parallel plate.
For sample B, a delta viscosity (between the pre-dilution viscosity and the highest viscosity phase) at $10^{-1}$ $s^{-1}$ at 25 C. of 19500 Pa·s was measured.

Example 3 (Inventive)

An inventive sample C was formulated according to Table 2 below.

TABLE 3

| Concentration | Component |
|---|---|
| 26.30% | Brij 98 |
| 26.30% | Pluronic P-103 |
| 43.50% | SLES [70% active aq. soln.] |
| 4.00% | Water |

Example 4 (Inventive)

Inventive samples D to H may be formulated according to Table 4 below.

TABLE 4

| Ingredients | D | E | F | G | H |
|---|---|---|---|---|---|
| 70% SLES (aq. Soln.) | 30 | 30 | 42.5 | 43.5 | 42.0 |
| Polyquaternium-7 (1) | — | 0.5 | 0.5 | — | 0.5 |
| Silicone oil (2) | — | — | 1.0 | 0.5 | — |
| Cationic Guar (3) | — | — | 0.5 | — | 0.5 |
| Brij 98 | 30 | 28 | 39 | 26.3 | 27.0 |
| Pluronic P-105 | 30 | 28 | 13 | 26.2 | 27 |
| Perfume | 0.5 | 0.5 | 0.5 | 0.5 | 0.5 |
| DI Water | 9.5 | 13 | 3 | 3.0 | 2.5 |
| Total | 100 | 100 | 100 | 100 | 100 |

Notes:
(1) Merquat 550
(2) Dimethicone DC 200
(3) hydroxypropyl guar hydroxypropyltrimonium chloride

Example 5 (Comparative)

A comparative sample CC was formulated according to Table 5 below.

TABLE 5

| Concentration | Component |
|---|---|
| 85% | 70% Active SLES aq. soln. |
| 15% | 35% Active Coco Amido Propyl Betaine (CAPB) aq. soln. |
| 100% | Total |

Initial Viscosity of sample CC is 413 Pa · s at $10^{-1}$ $s^{-1}$ 25 C. as measured by an Ares Rheometer, 25 mm parallel plate.
Sample CC with 50% water added (50 grams of the composition and 50 grams water) has a viscosity of 3887 Pa · s at $10^{-1}$ $s^{-1}$ at 25 C. as measured by an Ares Rheometer, 25 mm parallel plate. Therefore, for sample CC, a delta viscosity (between the pre-dilutian viscosity and the highest viscosity phase) at $10^{-1}$ $s^{-1}$ at 25 C. of 3474 Pa · s was measured.

SAMPLE PREPARATION METHOD

Examples 1-3 and 5 were prepared as follows:

Respective compositions according to examples 1-3 and 5 were weighed into a glass beaker and mixed using an overhead mixer at 10 rpm and 25 C for 5 minutes or until well blended.

Methods:

A) Standard Viscosity Method

Measure the viscosity of the sample at $10^{-1}s^{-1}$ at 25 C using the Ares Rheometer, 25 mm parallel plate obtainable from TA Instruments in Delaware, USA or an equivalent thereof.

B) Delta Viscosity Method:

1. Measure the pre-dilution viscosity of the sample using the Standard Viscosity Method.

2. Add 50 gram of water to 50 gram of sample in a 250 ml glass beaker.

3. Blend the sample and added water for 5 minutes using an overhead mixer at 10 rpm and 25 C.

4. Measure the post dilution viscosity of the most viscous phase of the sample using the Standard Viscosity Method.

5. Calculate the delta viscosity by subtracting the pre-dilution viscosity from the post dilution viscosity of the most viscous phase.

C) Krafft point

The Krafft point of a surfactant is defined as the temperature (or more precisely, the narrow temperature range) above which the solubility of a surfactant rises sharply. At this temperature the solubility of the surfactant becomes equal to the critical micelle concentration. It may be determined by locating the abrupt change in slope of a graph of the logarithm of the solubility against temperature or 1/T or can be rapidly estimated using the rapid estimation procedure described below.

Krafft Point Determination

Make up a 10% by wt. solution of surfactant or other sample in water. If needed, heat the system to dissolve the sample completely. Transfer the clear solution to a glass test tube. Place the test tube in a beaker equipped with a stirrer and filled with sufficient water to evenly cool the surfactant or sample solution. The solution should be cooled with continuous stirring and the temperature should be continuously recorded. Note the temperature when the crystallization process begins such that the solution becomes turbid. This temperature is taken as the Krafft point. If the crystallization temperature is below room temperature, add ice to the beaker to cool the test tube below room temperature to measure the subambient Krafft point.

D) Determination of Volume Percent of Liquid Crystal Structured Phase.

Place the sample in a 50 ml test tube with volume graduations. Centrifuge the sample for 30 minutes at 3000 rpm and 25 C. After centrifugation, the volume percent occupied by the separated liquid crystal phase can be calculated by dividing the volume occupied by the separated liquid crystal phase by the total sample volume and multiplying by 100. If necessary, the separated liquid crystal phase can be identified by optical birefringence techniques or other techniques well known in the art. This phase is often more dense then the isotropic phase and is therefore usually at the bottom layer. If particles are present, these will also separate out during centrifugation and this separated particle layer may be separately accounted for in the calculation.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A dilution thickening cleansing composition in the form of either a solution, dispersion, emulsion or microemulsion, comprising:
   a. about 20 to 60% by wt. of total anionic surfactant(s);
   b. about 5 to 50% by wt. of total nonionic surfactant(s);
   c. about 5 to 80% by wt. of total water soluble block copolymer(s)
   d. 0 to about 40% by wt. of water;
   e. less than 50% by volume of a liquid crystal structured phase; and
   f. wherein the cleansing composition has at least one phase with a delta viscosity value of greater than about 10,000 Pa·s when blended with an equal amount of water as measured using the Standard Viscosity Method.

2. The composition of claim 1, further comprising about 0 to 10% by wt. of total hydrophilic emollient(s) and about 0 to 10% by wt. of total hydrophobic emollient(s), wherein the combined concentration of the hydrophilic emollient(s) and hydrophobic emollient(s) is not zero.

3. The cleansing composition of claim 1 wherein the water soluble block copolymer has a number average molecular weight range of from about 1,000 to 20,000.

4. The cleansing composition of claim 1 wherein at least one of the water soluble block copolymer(s) has the structure according to formula I:

(I) $HO(CH_2CH_2O)_x(CH(CH_3)CHH_2O)_y(CH_2CH_2O)_xH$ (wherein the average value of x is 10 or more and the average value of y is 30 or more.

5. The cleansing composition of claim 1 further comprising a ratio range of total hydrophobic to total hydrophilic emollient(s) of from 10 to 0.1.

6. The cleansing composition of claim 2 wherein the hydrophobic emollient(s) (skin conditioning agent(s)) are selected from glyceride oils, mineral oils, silicone oils or blends and derivatives thereof.

7. The cleansing composition of claim 1 wherein the anionic surfactants are selected from the class of surfactants with a Krafft temperature of less than 20° C.

8. The cleansing composition of claim 1 further comprising amphoteric surfactant wherein the ratio of amphoteric surfactant to anionic surfactant is from 1 to 10.

9. The composition of claim 1 further comprising at least 0.1% by wt. of an active agent.

10. A prefilled dispenser packaged product for dispensing a thickened cleansing composition, comprising:
    a. a chamber with at least one outlet; and
    b. the cleansing composition of claim 1 contained within the chamber.

11. The dispenser of claim 10 further containing an inlet adapted for admitting water into the chamber.

* * * * *